United States Patent
DeCarlo

(10) Patent No.: US 10,610,298 B2
(45) Date of Patent: Apr. 7, 2020

(54) MICROWAVE ABLATION INSTRUMENT WITH INTERCHANGEABLE ANTENNA PROBE

(71) Applicant: COVIDIEN LP, Mansfield, MA (US)

(72) Inventor: Arnold V. DeCarlo, Frederick, CO (US)

(73) Assignee: COVIDIEN LP, Mansfield, MA (US)

( * ) Notice: Subject to any disclaimer, the term of this patent is extended or adjusted under 35 U.S.C. 154(b) by 623 days.

(21) Appl. No.: 15/444,525

(22) Filed: Feb. 28, 2017

(65) Prior Publication Data

US 2017/0165004 A1 Jun. 15, 2017

Related U.S. Application Data

(63) Continuation of application No. 13/083,185, filed on Apr. 8, 2011, now Pat. No. 9,579,150.

(51) Int. Cl.
| | | |
|---|---|---|
| *A61B 18/18* | (2006.01) | |
| *A61B 18/00* | (2006.01) | |
| *A61B 17/00* | (2006.01) | |

(52) U.S. Cl.
CPC .......... *A61B 18/1815* (2013.01); *A61B 18/18* (2013.01); *A61B 2017/00473* (2013.01);
(Continued)

(58) Field of Classification Search
CPC .......... A61B 18/18; A61B 2017/00473; A61B 2018/183; A61B 2018/00172; A61B 2018/00577
See application file for complete search history.

(56) References Cited

U.S. PATENT DOCUMENTS

| | | |
|---|---|---|
| 3,439,680 A | 4/1969 | Thomas, Jr. |
| D223,367 S | 4/1972 | Kountz |
| | (Continued) | |

FOREIGN PATENT DOCUMENTS

| | | |
|---|---|---|
| CN | 1103807 C | 3/2003 |
| CN | 1882288 A | 12/2006 |
| | (Continued) | |

OTHER PUBLICATIONS

U.S. Appl. No. 13/043,665, filed Mar. 9, 2011, Richard A. Willyard.
(Continued)

*Primary Examiner* — Michael F Peffley
*Assistant Examiner* — Yasamin Ekrami

(57) ABSTRACT

A surgical ablation system features a source of ablation energy, a handle adapted to operably couple to the source of ablation energy, and an ablation probe adapted to operably couple to the handle. The handle includes a housing having a proximal end and a distal end, a hub included within the housing having a plenum defined therein, and a proximal feedline in fluid communication at a proximal end thereof with the plenum and joined at a distal end thereof to a first coupling member. The ablation probe includes a probe hypotube shaft having a proximal end and a distal end, a second coupling member disposed at a proximal end of the probe hypotube shaft adapted to operably couple with the first coupling member, a distal tip adapted to penetrate tissue. Ablation energy is deliverable by the ablation probe when the source of ablation energy is operably coupled to the handle and the handle is operably coupled to the ablation probe.

16 Claims, 15 Drawing Sheets

(52) U.S. Cl.
CPC ............ *A61B 2018/00023* (2013.01); *A61B 2018/00172* (2013.01); *A61B 2018/00178* (2013.01); *A61B 2018/00577* (2013.01); *A61B 2018/183* (2013.01); *A61B 2018/1823* (2013.01)

(56) References Cited

U.S. PATENT DOCUMENTS

| | | |
|---|---|---|
| 3,938,527 A | 2/1976 | Rioux et al. |
| D263,020 S | 2/1982 | Rau, III |
| D266,842 S | 11/1982 | Villers et al. |
| D278,306 S | 4/1985 | McIntosh |
| D295,893 S | 5/1988 | Sharkany et al. |
| D295,894 S | 5/1988 | Sharkany et al. |
| 5,312,400 A | 5/1994 | Bales et al. |
| 5,336,220 A | 8/1994 | Ryan et al. |
| 5,348,554 A | 9/1994 | Imran et al. |
| D354,218 S | 1/1995 | Van de Peer |
| 5,599,346 A | 2/1997 | Edwards et al. |
| 5,609,151 A | 3/1997 | Mulier et al. |
| 5,658,278 A | 8/1997 | Imran et al. |
| 5,674,218 A | 10/1997 | Rubinsky et al. |
| D424,693 S | 5/2000 | Pruter |
| D424,694 S | 5/2000 | Tetzlaff et al. |
| D425,201 S | 5/2000 | Tetzlaff et al. |
| 6,139,570 A | 10/2000 | Saadat et al. |
| 6,146,380 A | 11/2000 | Racz et al. |
| 6,162,216 A | 12/2000 | Guziak et al. |
| D449,886 S | 10/2001 | Tetzlaff et al. |
| D457,958 S | 5/2002 | Dycus et al. |
| D457,959 S | 5/2002 | Tetzlaff et al. |
| 6,402,742 B1 | 6/2002 | Blewett et al. |
| 6,506,189 B1 | 1/2003 | Rittman, III et al. |
| 6,526,320 B2 | 2/2003 | Mitchell |
| 6,560,470 B1 | 5/2003 | Pologe |
| 6,575,969 B1 | 6/2003 | Rittman, III et al. |
| 6,605,085 B1 | 8/2003 | Edwards |
| D487,039 S | 2/2004 | Webster et al. |
| 6,706,040 B2 | 3/2004 | Mahon et al. |
| 6,752,805 B2 | 6/2004 | Maguire et al. |
| D496,997 S | 10/2004 | Dycus et al. |
| D499,181 S | 11/2004 | Dycus et al. |
| D525,361 S | 7/2006 | Hushka |
| D531,311 S | 10/2006 | Guerra et al. |
| D533,942 S | 12/2006 | Kerr et al. |
| D535,027 S | 1/2007 | James et al. |
| 7,186,222 B1 | 3/2007 | Callister et al. |
| 7,197,349 B2 | 3/2007 | Taimisto et al. |
| D541,418 S | 4/2007 | Schechter et al. |
| D541,938 S | 5/2007 | Kerr et al. |
| 7,270,656 B2 | 9/2007 | Gowda et al. |
| 7,294,127 B2 | 11/2007 | Leung et al. |
| D564,662 S | 3/2008 | Moses et al. |
| 7,387,631 B2 | 6/2008 | Durgin et al. |
| D576,932 S | 9/2008 | Strehler |
| D594,736 S | 6/2009 | Esjunin |
| D594,737 S | 6/2009 | Kelly et al. |
| D606,203 S | 12/2009 | Husheer et al. |
| D613,412 S | 4/2010 | DeCarlo |
| 7,846,158 B2 | 12/2010 | Podhajsky |
| 7,879,031 B2 | 2/2011 | Peterson |
| D634,010 S | 3/2011 | DeCarlo |
| 8,059,059 B2 | 11/2011 | Bonn |
| 8,361,062 B2 | 1/2013 | Bonn |
| 9,579,150 B2 | 2/2017 | DeCarlo |
| 2001/0025174 A1 | 9/2001 | Daniel et al. |
| 2002/0019627 A1 | 2/2002 | Maguire et al. |
| 2003/0060813 A1 | 3/2003 | Loeb et al. |
| 2003/0181901 A1 | 9/2003 | Maguire et al. |
| 2003/0195496 A1 | 10/2003 | Maguire et al. |
| 2004/0151562 A1 | 8/2004 | Hofmeister et al. |
| 2005/0015081 A1 | 1/2005 | Turovskiy et al. |
| 2005/0234443 A1 | 10/2005 | Rioux et al. |
| 2005/0245920 A1 | 11/2005 | Vitullo et al. |
| 2006/0259024 A1 | 11/2006 | Turovskiy et al. |
| 2007/0021743 A1 | 1/2007 | Rioux et al. |
| 2007/0073285 A1 | 3/2007 | Peterson |
| 2007/0078453 A1 | 4/2007 | Johnson et al. |
| 2007/0078454 A1 | 4/2007 | McPherson |
| 2007/0213703 A1 | 9/2007 | Naam et al. |
| 2007/0249936 A1 | 10/2007 | Deckman et al. |
| 2007/0250053 A1 | 10/2007 | Fernald et al. |
| 2007/0265609 A1 | 11/2007 | Thapliyal et al. |
| 2008/0027424 A1 | 1/2008 | DeCarlo et al. |
| 2008/0135217 A1 | 6/2008 | Turovskiy et al. |
| 2008/0243214 A1 | 10/2008 | Koblish |
| 2009/0131790 A1 | 5/2009 | Munrow et al. |
| 2009/0187180 A1 | 7/2009 | Brannan |
| 2009/0222002 A1 | 9/2009 | Bonn et al. |
| 2009/0295674 A1 | 12/2009 | Bonn |
| 2009/0299355 A1 | 12/2009 | Bencini et al. |
| 2010/0053015 A1 | 3/2010 | Willyard |
| 2010/0097284 A1 | 4/2010 | Brannan et al. |
| 2010/0152729 A1 | 6/2010 | Gallo, Sr. et al. |
| 2010/0168624 A1 | 7/2010 | Sliwa |
| 2010/0168729 A1 | 7/2010 | Wang et al. |
| 2010/0191236 A1 | 7/2010 | Johnson et al. |
| 2010/0286681 A1 | 11/2010 | Podhajsky |
| 2011/0046621 A1 | 2/2011 | Poshajsky |
| 2011/0060326 A1 | 3/2011 | Smith et al. |
| 2011/0066144 A1 | 3/2011 | Bonn et al. |
| 2011/0071582 A1 | 3/2011 | Willyard et al. |
| 2011/0077498 A1 | 3/2011 | McDaniel |
| 2011/0077633 A1 | 3/2011 | Bonn et al. |
| 2012/0265192 A1 | 10/2012 | Sliwa et al. |
| 2013/0190756 A1 | 7/2013 | Rioux et al. |
| 2013/0197491 A1 | 8/2013 | Golden et al. |
| 2013/0296699 A1 | 11/2013 | Deckman et al. |

FOREIGN PATENT DOCUMENTS

| | | |
|---|---|---|
| CN | 201642316 U | 11/2010 |
| CN | 101932358 A | 12/2010 |
| DE | 390937 C | 3/1924 |
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |

(56) References Cited

FOREIGN PATENT DOCUMENTS

| | | |
|---|---|---|
| DE | 102004022206 A1 | 12/2005 |
| DE | 202005015147 U1 | 2/2006 |
| EP | 246350 A1 | 11/1987 |
| EP | 0521264 A2 | 1/1993 |
| EP | 556705 A1 | 8/1993 |
| EP | 0558429 A1 | 9/1993 |
| EP | 608609 A2 | 8/1994 |
| EP | 0648515 A1 | 4/1995 |
| EP | 836868 A2 | 4/1998 |
| EP | 882955 A1 | 12/1998 |
| EP | 1159926 A3 | 3/2003 |
| EP | 2177173 A1 | 4/2010 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 55106 | 1/1993 |
| JP | 0540112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | H09500804 A | 1/1997 |
| JP | 11244298 A | 9/1999 |
| JP | 2000342599 A | 12/2000 |
| JP | 2000350732 A | 12/2000 |
| JP | 20018944 | 1/2001 |
| JP | 200129356 | 2/2001 |
| JP | 2001128990 A | 5/2001 |
| JP | 2001231870 A | 8/2001 |
| JP | 2007535370 A | 12/2007 |
| JP | 2008142467 A | 6/2008 |
| SU | 166452 | 1/1965 |
| SU | 407367 A1 | 10/1973 |
| SU | 727201 A2 | 4/1980 |
| WO | 9634571 A1 | 11/1996 |
| WO | 9724074 A1 | 7/1997 |
| WO | 0054682 A1 | 9/2000 |
| WO | 0174252 A2 | 10/2001 |
| WO | 200546753 A2 | 5/2005 |
| WO | 2006105121 A2 | 10/2006 |
| WO | 2009094422 A1 | 7/2009 |
| WO | 2010035831 A1 | 4/2010 |
| WO | 2011063061 A2 | 5/2011 |

OTHER PUBLICATIONS

U.S. Appl. No. 13/043,694, filed Mar. 9, 2011, Richard A. Willyard.
U.S. Appl. No. 13/050,729, filed Mar. 17, 2011, Casey M. Ladtkow.
U.S. Appl. No. 13/083,185, filed Apr. 8, 2011, Arnold V. DeCarlo.
U.S. Appl. No. 13/083,256, filed Apr. 8, 2011, Joseph D. Brannan.
U.S. Appl. No. 13/098,199, filed Apr. 29, 2011, Roop L. Mahajan.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product Instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw Hill, vol. 111, (1984), pp. 2490-2499.
Cosman et al., "Radiofrequency Lesion Generation and its Effect on Tissue Impedence", Applied Neurophysiology, 51:230-242. 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.

(56) References Cited

OTHER PUBLICATIONS

Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure. TM. Vessel Sealing System: A Case Report" Innovations That Work, Feb. 2002.
Humphries Jr. et al., "Finite.Element Codes to Model Electrical Heating and Non.cndot.L1near Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure.TM. Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure.TM. Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Canadian Office Action issued in Appl. No. CA 2,773,415 dated Dec. 5, 2017 (5 pages).
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report Application No. 12 002 536.6 dated Jul. 16, 2012. (8 pages).
U.S. Appl. No. 08/136,098, filed Oct. 14, 1993, Roger A. Stern.
U.S. Appl. No. 08/483,742, filed Jun. 7, 1995, Roger A. Stern.
U.S. Appl. No. 12/619,323, filed Nov. 16, 2009, Arnold V. DeCarlo.
U.S. Appl. No. 12/619,462, filed Nov. 16, 2009, Casey M. Ladtkow.
U.S. Appl. No. 12/620,289, filed Nov. 17, 2009, Joseph D. Brannan.
U.S. Appl. No. 12/642,623, filed Dec. 18, 2009, Prakash Manley.
U.S. Appl. No. 12/686,726, filed Jan. 13, 2010, Joseph D. Brannan.
U.S. Appl. No. 12/692,856, filed Jan. 25, 2010, Joseph D. Brannan.
U.S. Appl. No. 12/696,671, filed Jan. 29, 2010, Steven Kim.
U.S. Appl. No. 12/696,966, filed Jan. 29, 2010, Steven Kim.
U.S. Appl. No. 12/701,030, filed Feb. 5, 2010, Francesca Rossetto.
U.S. Appl. No. 12/708,974, filed Feb. 19, 2010, Joseph D. Brannan.
U.S. Appl. No. 12/709,014, filed Feb. 19, 2010, Joseph D. Brannan.
U.S. Appl. No. 12/712,864, filed Feb. 25, 2010, Joseph D. Brannan.
U.S. Appl. No. 12/713,429, filed Feb. 26, 2010, Anthony C. Lee.
U.S. Appl. No. 12/713,515, filed Feb. 26, 2010, Anthony C. Lee.
U.S. Appl. No. 12/713,641, filed Feb. 26, 2010, Anthony C. Lee.
U.S. Appl. No. 12/719,657, filed Mar. 8, 2010, Mani N. Prakash.
U.S. Appl. No. 12/722,034, filed Mar. 11, 2010, Casey M. Ladtkow.
U.S. Appl. No. 12/731,367, filed Mar. 25, 2010, Joseph D. Brannan.
U.S. Appl. No. 12/732,508, filed Mar. 26, 2010, Steven Kim.
U.S. Appl. No. 12/732,521, filed Mar. 26, 2010, Steven Kim.
U.S. Appl. No. 12/772,675, filed May 3, 2010, Brian Shiu.
U.S. Appl. No. 12/777,984, filed May 11, 2010, Joseph D. Brannan.
U.S. Appl. No. 12/786,671, filed May 25, 2010, Richard A. Willyard.
U.S. Appl. No. 12/787,639, filed May 26, 2010, Mani N. Prakash.
U.S. Appl. No. 12/792,904, filed Jun. 3, 2010, Ronald J. Podhajsky.
U.S. Appl. No. 12/792,932, filed Jun. 3, 2010, Ronald J. Podhajsky.
U.S. Appl. No. 12/792,947, filed Jun. 3, 2010, Ronald J. Podhajsky.
U.S. Appl. No. 12/792,970, filed Jun. 3, 2010, Ronald J. Podhajsky.
U.S. Appl. No. 12/793,037, filed Jun. 3, 2010, Ronald J. Podhajsky.
U.S. Appl. No. 12/823,211, filed Jun. 25, 2010, Mani N. Prakash.
U.S. Appl. No. 12/826,897, filed Jun. 30, 2010, Brian Shiu.
U.S. Appl. No. 12/826,902, filed Jun. 30, 2010, Brian Shiu.
U.S. Appl. No. 12/837,820, filed Jul. 16, 2010, Joseph D. Brannan.
U.S. Appl. No. 12/839,023, filed Jul. 19, 2010, Ronald J. Podhajsky.
U.S. Appl. No. 12/861,333, filed Aug. 23, 2010, Joseph D. Brannan.
U.S. Appl. No. 12/944,951, filed Nov. 12, 2010, Joseph D. Brannan.
U.S. Appl. No. 12/977,390, filed Dec. 23, 2010, Joseph D. Brannan.
U.S. Appl. No. 12/977,415, filed Dec. 23, 2010, Joseph D. Brannan.
U.S. Appl. No. 12/985,124, filed Jan. 5, 2011, Joseph D. Brannan.
U.S. Appl. No. 12/985,136, filed Jan. 5, 2011, Joseph D. Brannan.
U.S. Appl. No. 12/985,155, filed Jan. 5, 2011, Joseph D. Brannan.

(56) References Cited

OTHER PUBLICATIONS

U.S. Appl. No. 12/985,179, filed Jan. 5, 2011, Joseph D. Brannan.
U.S. Appl. No. 13/020,562, filed Feb. 3, 2011, Joseph D. Brannan.
U.S. Appl. No. 13/020,664, filed Feb. 3, 2011, Kenlyn S. Bonn.
U.S. Appl. No. 13/024,041, filed Feb. 9, 2011, Joseph D. Brannan.
U.S. Appl. No. 13/029,521, filed Feb. 17, 2011, Joseph D. Brannan.
U.S. Appl. No. 13/029,594, filed Feb. 17, 2011, Joseph D. Brannan.
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12:876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General, Gynecologic, Urologic, and Laparaoscopic Surgery. Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure. TM. Vessel Sealing System and LigaSure.TM. Atlas 20 cm Open Instrument" Innovations That Work, Jun. 2003.
Muller et al., "Extended Left Hemicolectomy Using the LigaSure. TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences.cndot.Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology. pp. 195-203.
Strasberg et al., "Use of a Bipolar Vassel-Sealing Device for Parenchymal Transection During Liver Surgery" Journal of Gastrointestinal Surgery, vol. 6. No. 4. Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.cndot.825.
Urologix, Inc.—Medical Professionals: Targis.TM. Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.

(56) References Cited

OTHER PUBLICATIONS

International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.
Chinese Notification of the First Office Action with Search (with English Translation), dated Feb. 28, 2015, corresponding to Chinese Patent Application No. 201210169145.5; 23 total pages.
European Extended Search Report dated Jul. 23, 2015, corresponding to European Application No. 15163674.3; 4 pages.
Japanese Office Action (with English Translation), dated Nov. 17, 2015, corresponding to Japanese Patent Application No. 2012-087246; 9 total pages.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.

Chinese Office Action (with English translation) dated Apr. 18, 2017, corresponding to Chinese Application No. 201510927309; 12 total pages.
Canadian Office Action issued in Appl. No. CA 2,773,415 dated Oct. 9, 2018 (5 pages).
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Nov. 11, 2010.
European Search Report EP 10008139.7 extended dated Nov. 30, 2010.
European Search Report EP 10008140.5 extended dated Dec. 28, 2010.
European Search Report EP 10008850.9 extended dated Nov. 30, 2010.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10158944.8 extended dated Jun. 21, 2010.
European Search Report EP 10161722.3 extended dated Jun. 16, 2010.
European Search Report EP 10163235.4 dated Aug. 10, 2010.
European Search Report EP 10185413.1 dated Dec. 7, 2010.

(56) References Cited

OTHER PUBLICATIONS

European Search Report EP 10185413.1 dated Mar. 14, 2011.
European Search Report EP 10191321.8 dated Apr. 7, 2011.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
Chinese Office Action, with English language translation, issued in Appl. No. CN 201510927309X, dated Nov. 3, 2017 (11 pages).

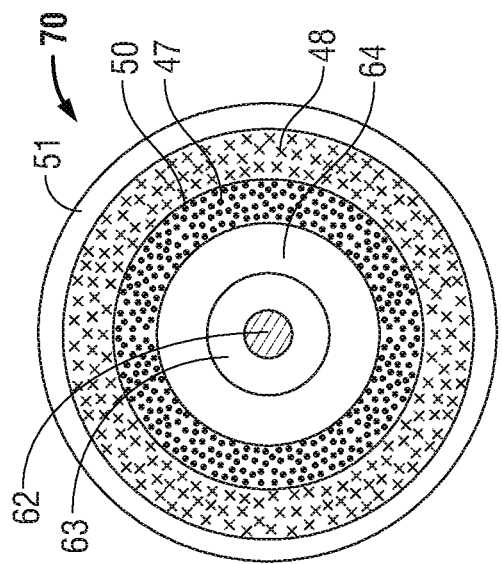
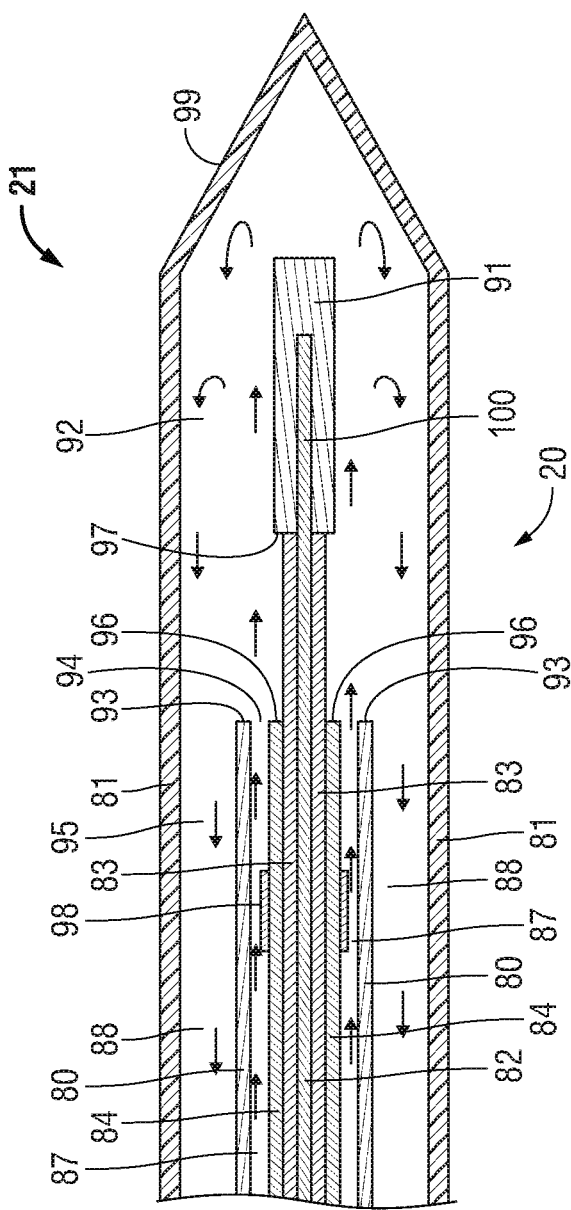

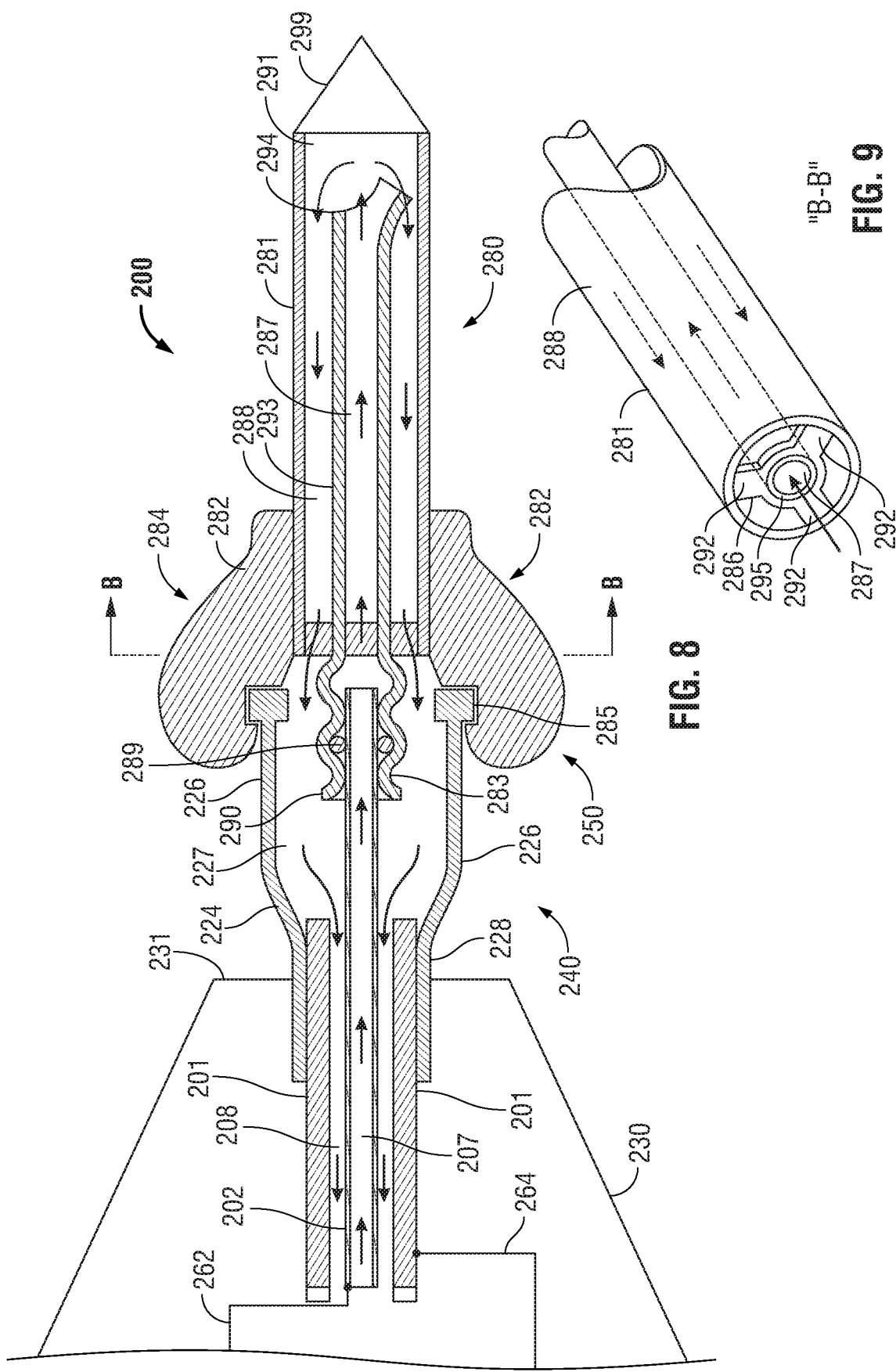

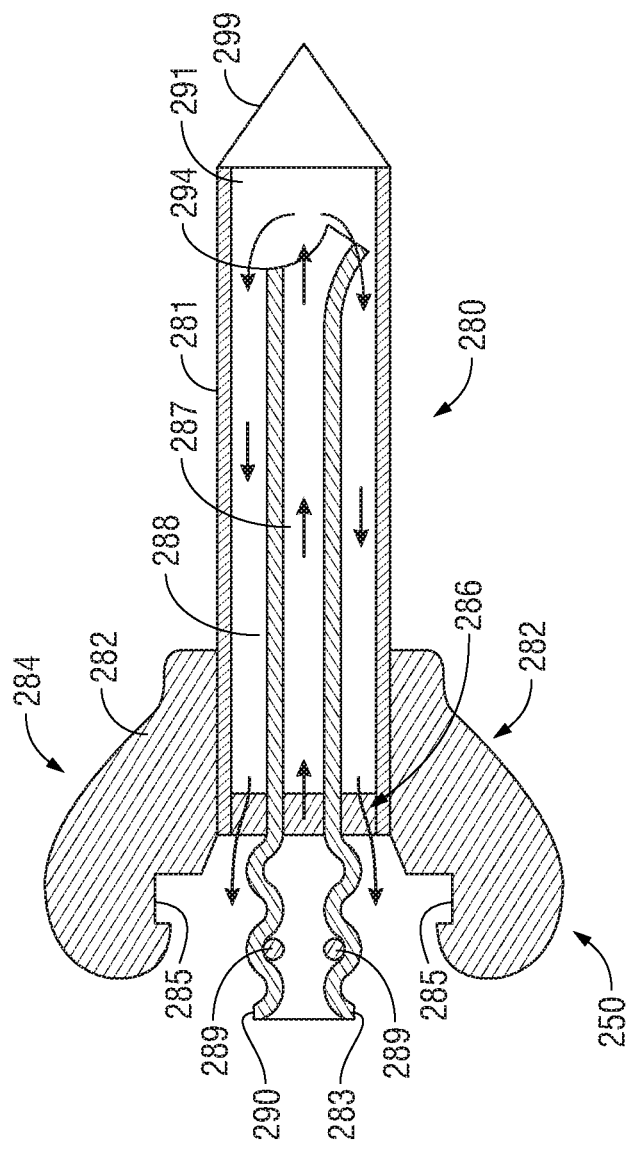

MICROWAVE ABLATION INSTRUMENT WITH INTERCHANGEABLE ANTENNA PROBE

CROSS-REFERENCE TO RELATED APPLICATIONS

The present application is a continuation application of U.S. patent application Ser. No. 13/083,185, filed on Apr. 8, 2011, the entire contents of which are incorporated by reference herein.

BACKGROUND

1. Technical Field

The present application relates to systems and methods for providing energy to biologic tissue and, more particularly, to an electrosurgical instrument adapted to perform tissue ablation having an interchangeable antenna probe.

2. Background of Related Art

Energy-based tissue treatment is well known in the art. Various types of energy (e.g., electrical, ultrasonic, microwave, cryogenic, thermal, laser, etc.) are applied to tissue to achieve a desired result. Electrosurgery involves application of high radio frequency electrical current to a surgical site to cut, ablate, coagulate or seal tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator. In tissue ablation electrosurgery, the radio frequency energy may be delivered to targeted tissue by an antenna or probe.

There are several types of microwave antenna assemblies in use, e.g., monopole, dipole and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors, which are linearly-aligned and positioned end-to-end relative to one another with an electrical insulator placed therebetween. Helical antenna assemblies include a helically-shaped conductor connected to a ground plane. Helical antenna assemblies can operate in a number of modes including normal mode (broadside), in which the field radiated by the helix is maximum in a perpendicular plane to the helix axis, and axial mode (end fire), in which maximum radiation is along the helix axis. The tuning of a helical antenna assembly may be determined, at least in part, by the physical characteristics of the helical antenna element, e.g., the helix diameter, the pitch or distance between coils of the helix, and the position of the helix in relation to the probe assembly to which it is mounted.

The typical microwave antenna has a long, thin inner conductor that extends along the longitudinal axis of the probe and is surrounded by a dielectric material and is further surrounded by an outer conductor around the dielectric material such that the outer conductor also extends along the axis of the probe. In another variation of the probe that provides for effective outward radiation of energy or heating, a portion or portions of the outer conductor can be selectively removed. This type of construction is typically referred to as a "leaky waveguide" or "leaky coaxial" antenna. Another variation on the microwave probe involves having the tip formed in a uniform spiral pattern, such as a helix, to provide the necessary configuration for effective radiation. This variation can be used to direct energy in a particular direction, e.g., perpendicular to the axis, in a forward direction (i.e., towards the distal end of the antenna), or combinations thereof. In the case of tissue ablation, a high radio frequency electrical current in the range of about 500 MHz to about 10 GHz is applied to a targeted tissue site to create an ablation volume, which may have a particular size and shape. Ablation volume is correlated to antenna design, antenna tuning, antenna impedance and tissue impedance.

Certain surgical procedures require multiple ablation probe placements. Needle probes that are frequently used in such procedures may become dull and bent, and consequently may become more difficult to place when reused. To address this concern, surgeons may utilize multiple probes during a surgical procedure. This approach may have drawbacks in that when multiple probes are place, the handles and cables associated with the multiple probes can be cumbersome to coordinate and manipulate at a surgical site. This, in turn, may lead to increased operative times and suboptimal surgical outcomes.

SUMMARY

The present disclosure is directed to a microwave ablation instrument having a handle portion and an interchangeable antenna probe. The replaceable probe may be reusable or disposable. The probe is adapted to operably connect to the handle using a connector configured to provide electrical and fluidic coupling between the handle and probe. The probe includes a monopole or dipole antenna assembly configured to deliver ablation energy to tissue. The handle is adapted to operable couple to a source of ablation energy, e.g., a generator. The handle may additionally or alternatively be configured to couple to a source of coolant. In use, a surgeon may insert one or more of the interchangeable probes into preselected regions of targeted tissue. The surgeon may then attach the handle to a first probe, activate the generator to deliver ablation energy to the first region of tissue, then move the handle to a second probe, and so forth, to deliver ablation energy to each pre-positioned probe in turn. In this manner, a single handle may be used to treat multiple regions of tissue without requiring repeated re-insertion of a single probe. In addition, use of a single handle with multiple interchangeable probes, rather than a multiple prior art handles each with a fixed probe, may significantly reduce the number of cables and clutter at the operative site, which benefits both surgeon and patient by streamlining procedures and improving operative outcomes.

The probe many include a monopole antenna, a dipole antenna, and variations thereof, such as without limitation, a wet-tip monopole antenna or a choked wet-tip dipole antenna.

A surgical ablation system in accordance with an embodiment of the present disclosure includes a source of ablation energy, a handle adapted to operably couple to the source of ablation energy, and an ablation probe adapted to operably couple to the handle. The handle includes a housing having a proximal end and a distal end, a hub included within the housing having a plenum defined therein, and a proximal feedline in fluid communication at a proximal end thereof with the plenum and joined at a distal end thereof to a first coupling member. The ablation probe includes a probe hypotube shaft having a proximal end and a distal end, a second coupling member disposed at a proximal end of the probe hypotube shaft adapted to operably couple with the first coupling member, a distal tip adapted to penetrate tissue. Ablation energy is deliverable by the ablation probe when the source of ablation energy is operably coupled to the handle and the handle is operably coupled to the ablation probe.

A disposable ablation probe in accordance with an embodiment of the present disclosure includes a probe hypotube shaft having a proximal end and a distal end, a probe inner conductor disposed along a longitudinal axis of the probe hypotube shaft, a probe insulator coaxially-disposed about probe inner conductor, a probe outer conductor coaxially disposed about probe insulator, and a probe coolant tube concentrically-disposed between the probe hypotube and the probe outer conductor to form a probe inflow conduit and a probe outflow conduit. A cooling chamber is defined within the distal end of the probe hypotube shaft and is in fluid communication with at least one of the probe inflow conduit or the probe outflow conduit. A coupling member is disposed at a proximal end of the probe hypotube shaft and is adapted to operably couple the probe to a handle. At a distal end of the hypotube shaft is a tip adapted to penetrate tissue.

An embodiment of a surgical instrument handle for use with a disposable ablation probe in accordance with the present disclosure includes a housing having a proximal end and a distal end, a hub included within the housing having a plenum defined therein, and a proximal feedline in fluid communication at a proximal end thereof with the plenum and joined at a distal end thereof to a first coupling member. The proximal feedline includes a feedline hypotube shaft having a proximal end and a distal end, a feedline inner conductor disposed along a longitudinal axis of the feedline, a feedline insulator coaxially-disposed about feedline inner conductor, a feedline outer conductor coaxially disposed about feedline insulator, and a feedline coolant tube concentrically-disposed between feedline hypotube and the feedline outer conductor to form a feedline inflow conduit and a feedline outflow conduit.

Also disclosed is an ablation system having a source of ablation energy operatively coupled to an ablation probe as described herein. The disclosed system may further include at least one of a source of coolant or a source of pressure operatively coupled to an ablation probe as described herein.

BRIEF DESCRIPTION OF THE DRAWINGS

The above and other aspects, features, and advantages of the present disclosure will become more apparent in light of the following detailed description when taken in conjunction with the accompanying drawings in which:

FIG. 6 shows a section view of a feedline of an ablation instrument having a removable probe in accordance with the present disclosure;

FIG. 7 shows an enlarged, cutaway view of a tip portion of an ablation instrument having a removable probe in accordance with the present disclosure;

FIG. 8 shows a side, cutaway view of another embodiment of a removable antenna assembly in accordance with the present disclosure;

FIG. 9 shows a section view of the FIG. 8 removable antenna assembly;

FIG. 11 shows a detailed side, cutaway view of a female connector of the FIG. 8 removable antenna assembly.

DETAILED DESCRIPTION

Figure 1:
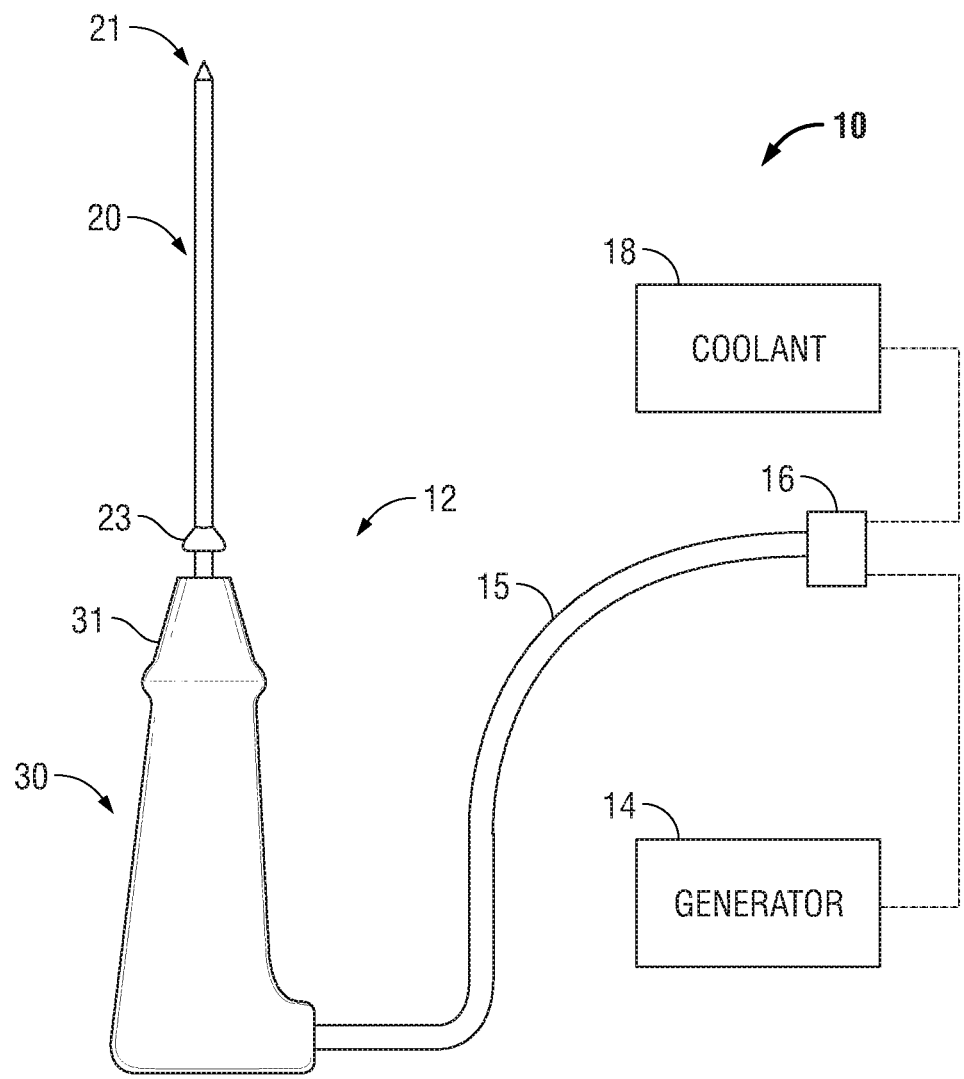
FIG. 1 shows a schematic diagram of an embodiment of an ablation system that includes a handle and a removable probe in accordance with the present disclosure.

Particular embodiments of the present disclosure are described hereinbelow with reference to the accompanying drawings; however, it is to be understood that the disclosed embodiments are merely examples of the disclosure, which may be embodied in various forms. Well-known functions or constructions and repetitive matter are not described in detail to avoid obscuring the present disclosure in unnecessary or redundant detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, shall refer to the end of the instrument that is closer to the user, while the term "distal" shall refer to the end that is farther from the user. In addition, as used herein, terms referencing orientation, e.g., "top", "bottom", "up", "down", "left", "right", "clockwise", "counterclockwise", and the like, are used for illustrative purposes with reference to the figures and features shown therein. It is to be understood that embodiments in accordance with the present disclosure may be practiced in any orientation without limitation. In this description, as well as in the drawings, like-referenced numbers represent elements which may perform the same, similar, or equivalent functions.

References to connector gender presented herein are for illustrative purposes only, and embodiments are envisioned wherein the various components described can be any of male, female, hermaphroditic, or sexless gender. Likewise, references to circular and coaxial connectors are illustrative in nature, and other connector types, shapes and configurations are contemplated within the scope of the present disclosure.

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3\times10^8$ cycles/second) to 300 gigahertz (GHz) ($3\times10^{11}$ cycles/second). As it is used in this description, "ablation procedure" generally refers to any ablation procedure, such as microwave ablation, radio frequency (RF) ablation, or microwave ablation assisted resection. As it is used in this description, "transmission line" generally refers to any transmission medium that can be used for the propagation of signals from one point to another.

Various embodiments of the present disclosure provide electrosurgical devices operably associated with directional reflector assemblies for treating tissue and methods of directing electromagnetic radiation to a target volume of tissue. Embodiments may be implemented using electromagnetic radiation at microwave frequencies, or, at other frequencies. An electrosurgical system having an aperture assembly that includes an energy applicator operably associated with a directional reflector assembly, according to various embodiments, is configured to operate between about 300 MHz and about 10 GHz with a directional radiation pattern.

Various embodiments of the presently disclosed electrosurgical devices, directional reflector assemblies, thereto and electrosurgical system including the same are suitable for microwave ablation and for use to pre-coagulate tissue for microwave ablation assisted surgical resection. Although various methods described hereinbelow are targeted toward microwave ablation and the destruction and/or resection of targeted tissue, it is to be understood that methods for directing electromagnetic radiation may be used with other therapies in which the target tissue is partially destroyed, damaged, or dissected, such as, for example, to prevent the conduction of electrical impulses within heart tissue. In addition, the teachings of the present disclosure may apply to a dipole, monopole, helical, or other suitable type of microwave antenna.

FIG. 1 shows an ablation system 10 in accordance with an embodiment of the present disclosure. The ablation system 10 includes an ablation instrument 12 that is operably connected by a cable 15 to connector 16, which further operably connects instrument 12 to a generator assembly 14. Generator assembly 14 may be a source of ablation energy, e.g., microwave or RF energy in the range of about 915 MHz to about 10.0 GHz. Instrument 12 is adapted for use in various surgical procedures and generally includes a handle assembly 30 configured to operably engage with an antenna probe 20. A proximal end 23 of probe 20 electromechanically engages a distal end 31 of handle 30. Cable 15 may additionally or alternatively provide a conduit (not explicitly shown in FIG. 1) configured to provide coolant from a coolant source 18 to ablation instrument 12.

Figure 2:
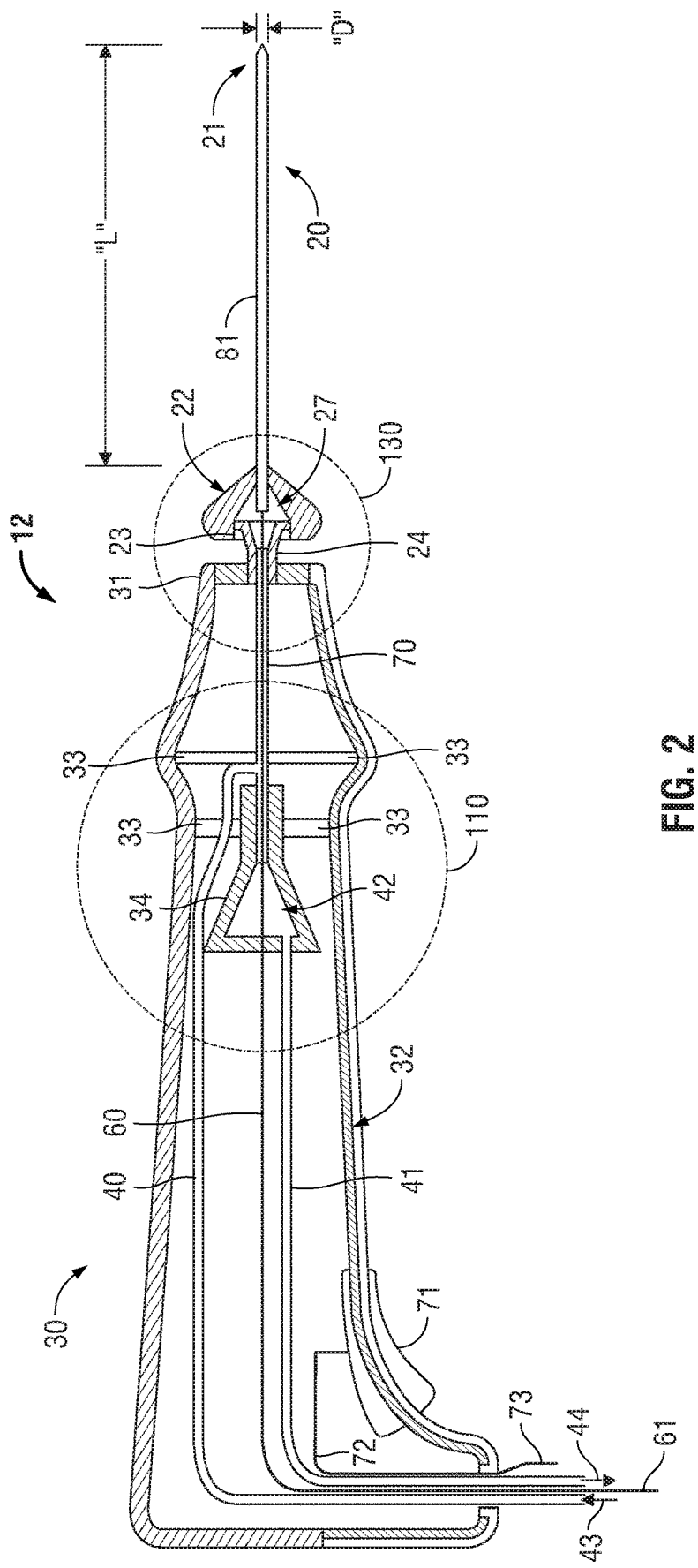
FIG. 2 shows a side, cutaway view of an ablation instrument having a handle and a removable probe in accordance with the present disclosure.
Figure 3:
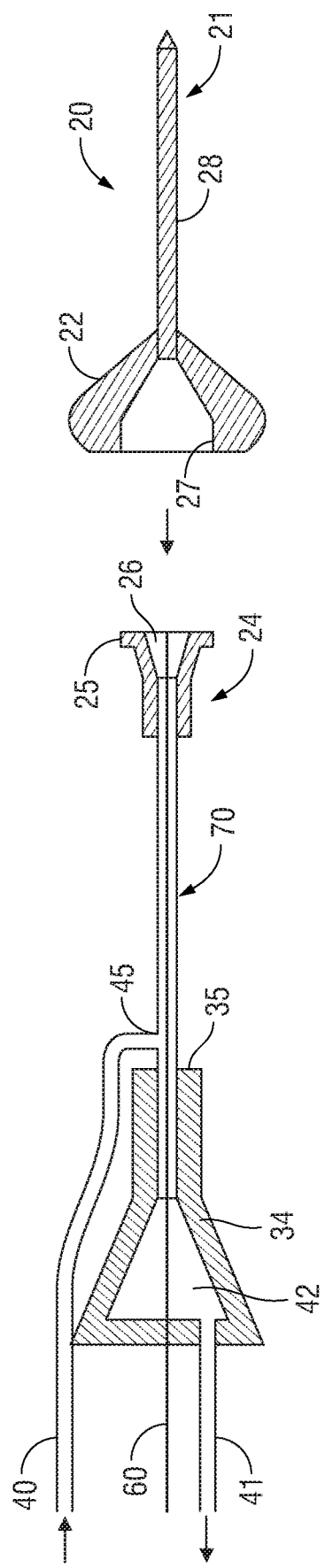
FIG. 3 shows a schematic view of the relationship between components of an ablation instrument having a removable probe in accordance with the present disclosure.
Figure 4:
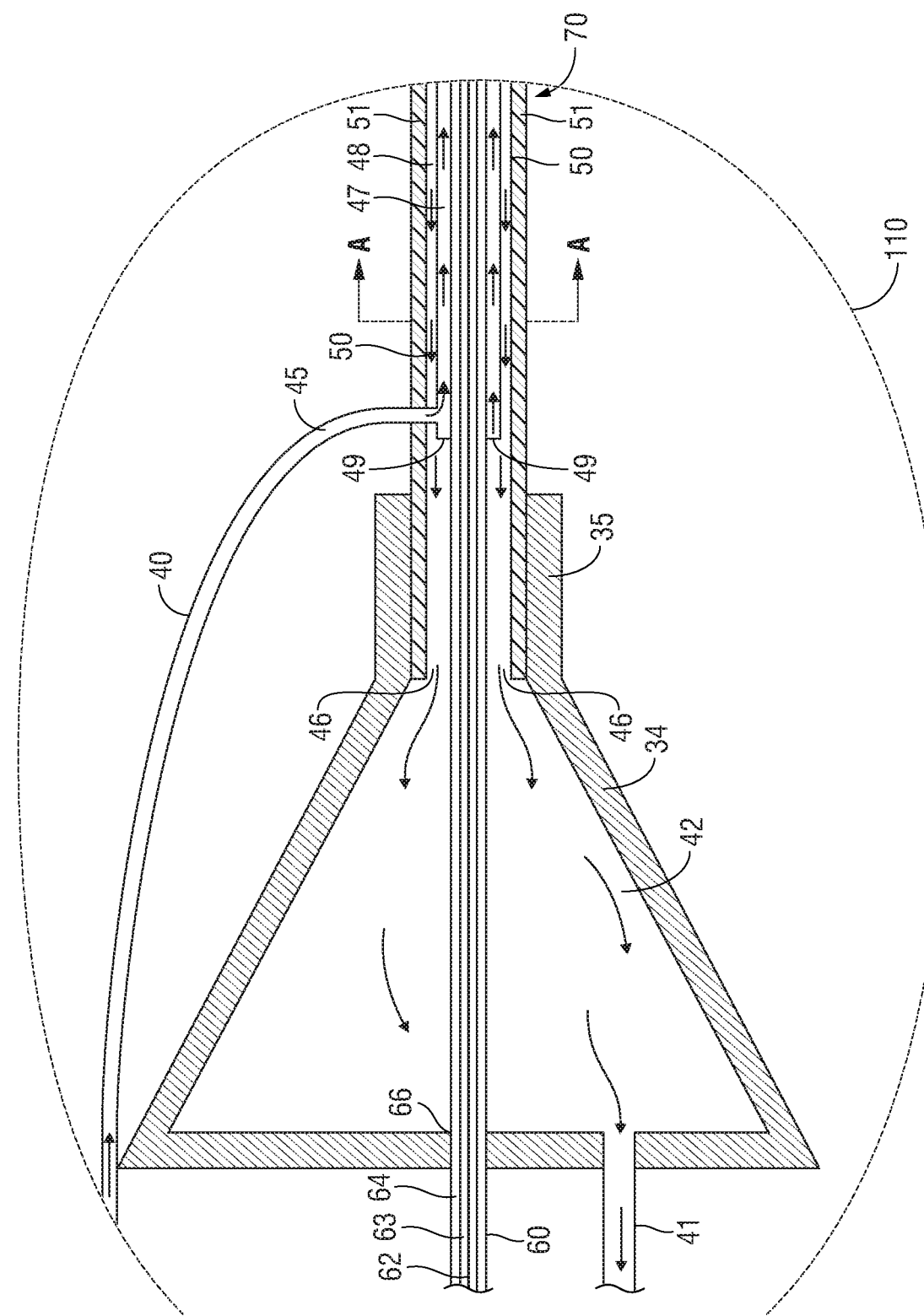
FIG. 4 shows an enlarged, cutaway view of a hub portion of an ablation instrument having a removable probe in accordance with the present disclosure.

Turning to FIGS. 2, 3, and 4, an embodiment of an ablation instrument in accordance with the present disclosure includes a handle 30 having a housing 32. Housing 32 may be assembled from a two piece (left and right half) clamshell-type assembly that is joined along a common edge by any suitable manner of attachment, e.g., laser welding, chemical welding, adhesive, mechanical fasteners, clips, threaded fasteners and the like. Housing 32 includes a hub 34 that couples a handle feedline 70 with an input cable 60, an inflow tube 40 and an outflow tube 41. Hub 34 includes a plenum 42 that receives spent coolant from a proximal end 46 of feedline outflow conduit 48, and from which spent coolant flows into outflow tube 41. Input cable 60 includes an inner conductor 62 coaxially disposed within an outer conductor 64 having an insulator 63 disposed therebetween.

Figure 5:
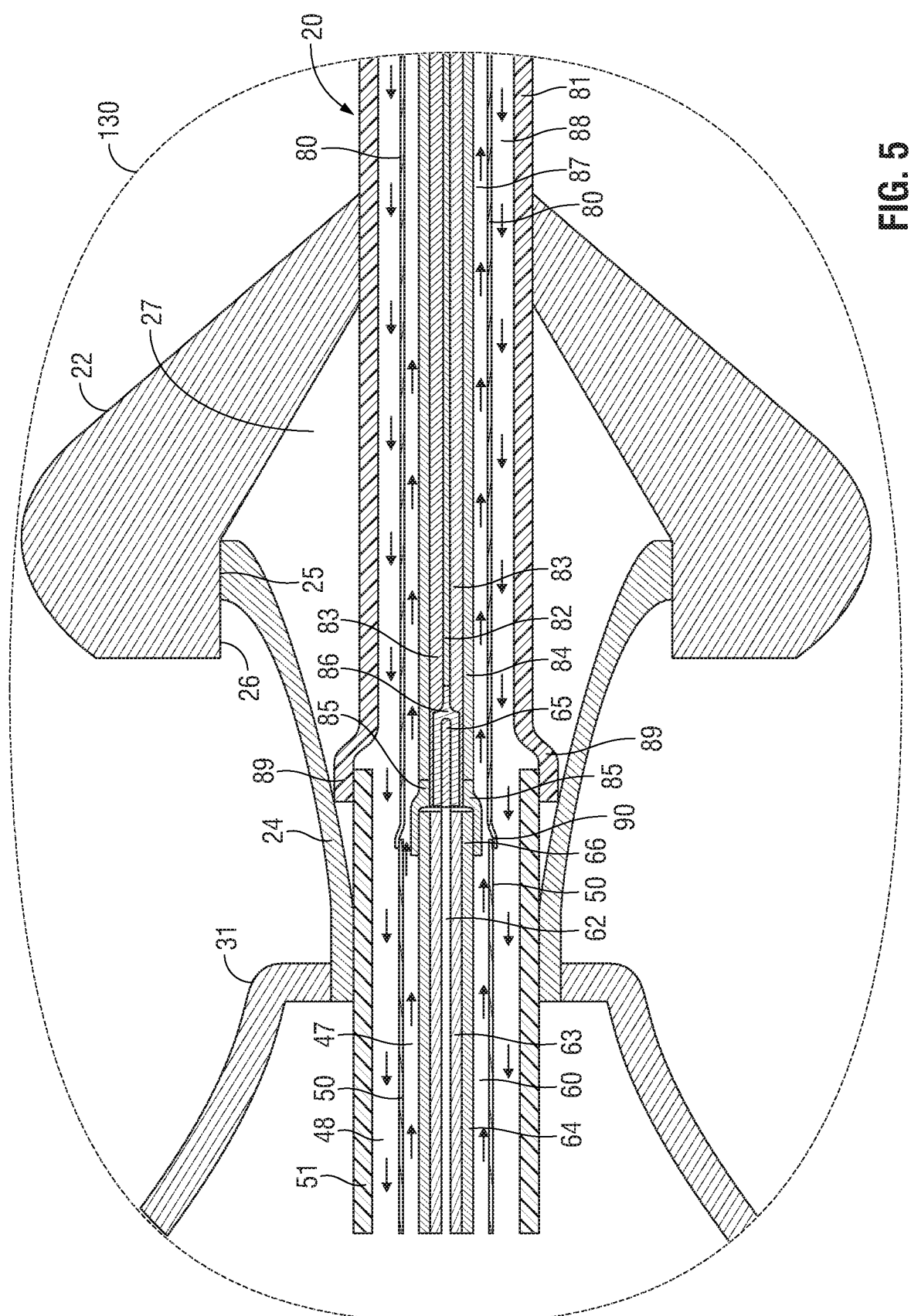
FIG. 5 shows an enlarged, cutaway view of a connector portion of an ablation instrument having a removable probe in accordance with the present disclosure.
Figure 10:
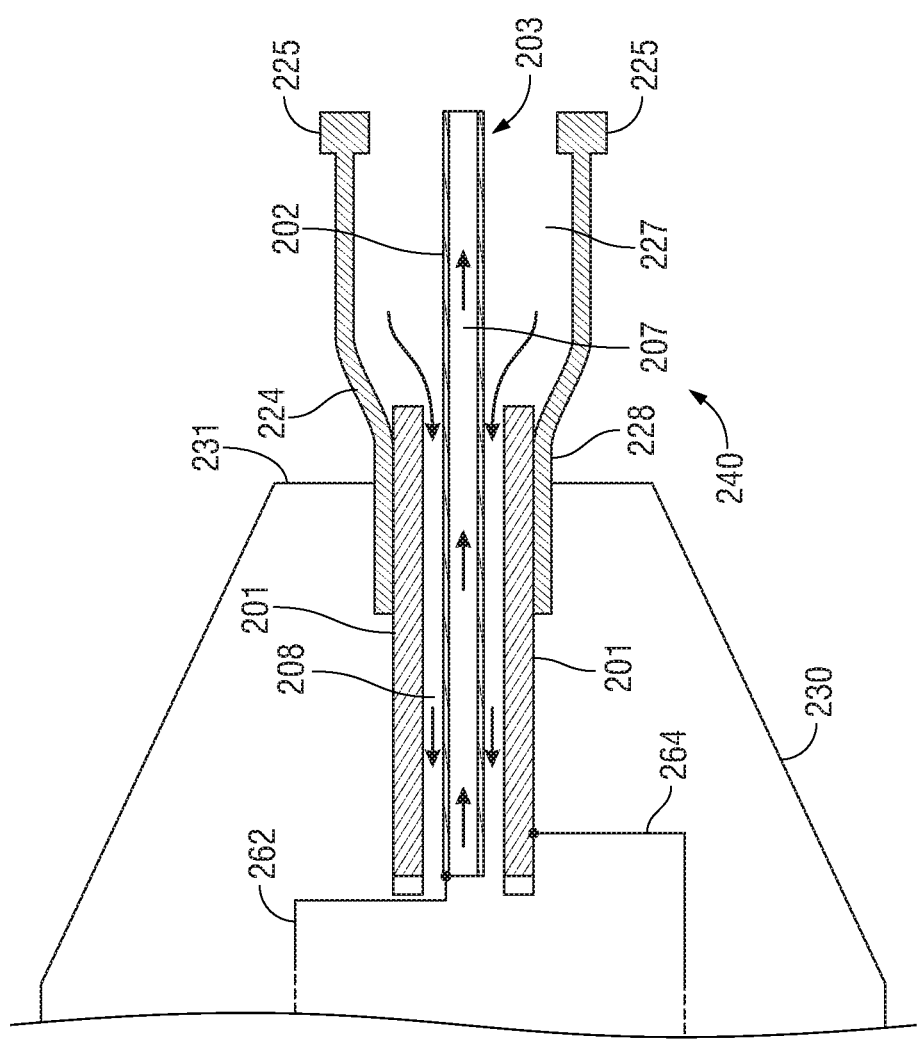
FIG. 10 shows a detailed side, cutaway view of a male connector of the FIG. 8 removable antenna assembly.

Proximal feedline 70 includes a number of elements arranged concentrically therein that are adapted to deliver electrosurgical energy and coolant to antenna probe 20 and to remove coolant from antenna probe 20. Proximal feedline 70 is formed from a feedline hypotube 51 that extends distally from a distal end 35 of hub 34 and terminates distally within male luer-style member 24, as shown in FIG. 5. Input cable 60 extends through a proximal wall of hub 34 via sealed port 66 and continues through plenum 42 and a longitudinal axis of feedline hypotube 51 and terminates distally within male luer-style member 24. As seen in FIG. 6, input cable 60 includes feedline inner conductor 62 disposed along a longitudinal axis thereof. A feedline insulator 63 is coaxially disposed about feedline inner conductor 62. A feedline outer conductor 64 is disposed about feedline insulator 63. A feedline coolant tube 50 is concentrically disposed between feedline hypotube 51 and input cable 60 to form a feedline inflow conduit 47 and a feedline outflow conduit 48. A proximal end 46 of feedline outflow conduit 48 is in fluid communication with plenum 42. A distal end 45 of inflow tube 40 is in fluid communication with a proximal end of feedline inflow conduit 47 to provide coolant during use to antenna probe 20. A seal 49 is disposed at a proximal end of feedline coolant tube 50 to direct inflowing fresh coolant distally through feedline inflow conduit 47 and to prevent intermingling of inflowing fresh coolant with spent coolant exiting through feedline outflow conduit 48. A distal end 65 of feedline inner conductor 62 extends beyond a distal end of cable 60 and is adapted to engage an inner conductor connector 86 to facilitate the electrical coupling of feedline inner conductor 62 with a probe inner conductor 82 when antenna probe 20 is joined to handle 30.

Handle 30 includes an actuator 71, which may be a handswitch as shown, or, alternatively, and without limitation, a trigger switch, a pushbutton switch, a slide switch, a lever switch, that is configured to activate generator 14 when actuated by a surgeon. Actuator 71 may be operably coupled to generator 14 by control cable 72 and/or control cable 73. In an embodiment, actuator 71 includes a momentary-contact, single pole single throw (SPST) switch. In an embodiment, actuator 71 may include a snap dome switch. An interlock (not explicitly shown) may be included in handle 30 to inhibit actuation of generator 14 when no antenna probe 20 is coupled to handle 30.

Antenna probe 20 includes a probe hypotube 81 shaft having an internal structure that generally corresponds to that of feedline hypotube 51 and includes features at a proximal end 23 thereof adapted to operatively engage a distal end of feedline hypotube 51. Hypotube 81 includes a probe inner conductor 82 that extends along a longitudinal axis of hypotube 81. A probe insulator 83 is coaxially-disposed about probe inner conductor 81, and a probe outer conductor 84 is coaxially-disposed about insulator 83. A probe coolant tube 80 is concentrically-disposed between probe hypotube 81 and probe outer conductor 84 to form a probe inflow conduit 87 and a probe outflow conduit 88.

An inner conductor connector 86 is operatively fixed to probe inner conductor 82 and is configured to operably engage feedline inner conductor 62 when antenna probe 20 is joined to handle 30. As shown, inner conductor connector 86 is configured as a female connector, however, inner conductor connector 86 may be a male connector, a hermaphroditic connector, or any other suitable form of connector. Probe outer conductor 84 includes an outer conductor connector 85 operatively fixed to a proximal end thereof that is configured to operably engage a proximal end 66 of feedline outer conductor 64 when antenna probe 20 is joined to handle 30.

The conductor connecters may be joined to their respective conductors (e.g., inner conductor connector 86 to probe inner conductor 82, and outer conductor connector 85 to outer conductor 84) by any suitable manner of electromechanical bonding, including without limitation soldering, brazing, welding, crimping, or threaded fastener. An outer conductor insulator (not explicitly shown) may be coaxially disposed about feedline outer conductor 64 and/or probe outer conductor 84.

A proximal end of probe hypotube 81 includes a hypotube flared section 89 that is configured to form a fluid-tight connection around a distal end of feedline hypotube 51. A proximal end of probe coolant tube 80 includes a coolant tube flared section 90 that is configured to form a fluid-tight connection around a distal end of feedline coolant tube 50. In an embodiment, the mating surfaces between feedline hypotube 51 and hypotube flared section 89, and between feedline coolant tube 50 and coolant tube flared section 90 may include seal-enhancing elements (not explicitly shown), including without limitation an o-ring, elastomeric coating, a lubricious coating, or a series of interlocking ridges. In an embodiment, the flared sections, i.e., hypotube flared section 89 and/or coolant tube flared section 90, may be configured to expand upon the insertion of the corresponding mating proximal component, i.e., feedline hypotube 51 and/or feedline coolant tube 50, respectively, which, in turn, provides improved sealing between the joined components.

The handle 30 and antenna probe include coupling elements 24 and 22, respectively, that are adapted to operatively couple handle 30 and probe 20. More particularly, and as seen in FIGS. 5 and 6, handle 30 includes a male luer-style member 24 that is configured to operably engage a female luer-style collar 22. When coupled, an outer mating surface 25 of male luer member 24 engages an inner mating surface 26 of female luer collar 22 to retain antenna probe 20 to handle 30 in a fixed relationship. In an embodiment, male luer member 24 engages an inner mating surface 26 of female luer collar 22 by frictional retention. In other envisioned embodiments within the scope of the present disclosure, male luer member 24 engages female luer collar 22 by any suitable manner of connection, including without limitation, threaded engagement, bayonet mount (e.g., "half-twist" connector), quick disconnect connector (MPT-FTP pair), and the like.

While in the example embodiment the coupling elements 24 and 22 are male and female couplers, respectively, embodiments in accordance with the present disclosure may utilize any combination of cooperative male, female, and hermaphroditic couplers 24 and 22 to effectuate operative coupling of handle 30 and probe 20.

Turning now to FIG. 7, hypotube 81 extends distally and includes a distal tip 21 having a contour configured to facilitate piercing of tissue. As shown, tip 21 includes a generally conical tapered section 99, however, other tip configurations are within the scope of the present disclosure, including without limitation, chisel tip, flat tip, spoon tip, and so forth. A cooling chamber 92 is defined within tip 21 to facilitate the circulation of coolant therein and to control the temperature of probe 20. A distal end 93 of probe coolant tube 80 defines a coolant inflow port 94 through which coolant flows form probe inflow conduit 87 into coolant chamber 92. A distal end 93 of probe coolant tube 80 also defines coolant outflow port 95, that is arranged generally concentrically about coolant inflow port 94, and through which spent coolant flows from coolant chamber 92 proximally into probe outflow conduit 88.

Probe insulator 83 and probe inner conductor 82 extend distally beyond a distal end 93 of coolant tube 80 and/or a distal end 96 of probe outer conductor 84 into cooling chamber 92. A distal end 100 of inner conductor 82 extends distally beyond a distal end 97 of probe insulator 83 into distal radiating section 91. Distal radiating section 91 is electromechanically coupled to the distal end 100 of probe inner conductor 82 by any suitable manner of attachment, including without limitation soldering, welding, brazing, crimping, and the like. A quarter wave balun 98 may be coaxially disposed about outer conductor 98 to form a quarter-wave short-circuiting balun adapted to contain the radiated microwave energy to the region of tip 21.

An ablation probe 20 in accordance with the present disclosure may have a length L that ranges from about 1 cm to about 1 m in length. During a surgical procedure, a surgeon may elect to use one or more ablation probes, in one or more lengths, in order to achieve the desired surgical outcome. The diameter D of an ablation probe in accordance with the present disclosure may have a range of about 0.1 mm to about 10 mm.

In an embodiment, a kit that includes a handle assembly 30 and a plurality of ablation probes 20 may be provided to a surgeon. The quantity, length, and/or diameter of the ablation probes provided in the kit may be based at least in part by a particular surgical procedure for which the kit may be suited. The kit may be provided in sterile packaging to ensure the handle 30 and probes 20 are provided to the surgical site free of biocontaminants.

Another example embodiment according to the present disclosure is illustrated in FIGS. 8-11. An antenna assembly 200 includes a handle-side coupler 240 and an antenna probe 280. A proximal end 284 of probe 280 may be selectively and releasably engageable with the handle assembly 231 or a portion thereof, e.g., coupler 240. Antenna probe 280 may be considered disposable, reusable, and may be referred to by the portmanteau "reposable." Accordingly, a new or different probe 280 may selectively replace a prior-coupled probe 280 as required.

Hypotube 210 is fixed within a handle 230. Hypotube 230 may be formed from any suitable material capable of delivering fluid and/or capable of conducting electricity, such as without limitation, stainless steel. Hypotube 201 may be operably coupled to a source of electrosurgical energy by a conductor 264. Coupler 240 includes a male connector 224 that is fixed to a distal end 231 of handle 230. Male connector 224 may be a luer-style connector formed from an electrically conductive, rigid material including without limitation, stainless steel. Male connector 224 is electrically coupled to hypotube 201. In one aspect, the combination of conductor 264, hypotube 201, and/or connector 224 are adapted to deliver electrosurgical energy to probe 280, as will be further described in detail below.

Connector 225 includes a proximal base portion 228 having a diameter that is configured to fixably engage hypotube 201 around an outer diameter thereof to form an electrically-conductive and fluid-tight connection therewith. Proximal base portion 228 of connector 224 may extend proximally into handle 230, which may increase the rigidity and junction strength of the overall antenna assembly 200. A flared distal portion 226 of connector 224 having a diameter greater than that of proximal base portion 228 forms an internal plenum volume 227 to accommodate the flow of coolant exiting from antenna probe 280, and includes a distal rim 225 configured to selectively engage a corresponding circumferential saddle 285 defined within a female connector 282 that is fixed at a proximal end 284 of probe 280.

A coolant tube 202 is positioned concentrically within hypotube 201. The inner portion of coolant tube 202 defines an inflow conduit 207 that is adapted to deliver coolant from a coolant source (not explicitly shown in this view), that may be operably coupled to a proximal end of coolant tube 202, to probe assembly 280. An outflow conduit 208 is defined by the coaxial arrangement of coolant tube 202 and hypotube 201, and is in fluid communication with plenum 277 to receive spent coolant exiting from probe 280. Coolant tube 202 may be formed from any suitable material, however it is envisioned coolant tube 202 is formed from conductive material. Coolant tube 202 may be operably coupled to a source of electrosurgical energy by a conductor 262. By this arrangement, coolant tube 202 may be adapted to provide electrosurgical energy to probe 280. Coolant tube 202 extends distally to about a plane defined by a distal rim 225 of connector 224.

Probe 280 includes a number of features designed to facilitate the selective operable engagement with coupler 240. Female coupler 250 includes a female connector 282 that is fixed to a proximal end 284 of probe 280. Female connector 282 may be a luer-style connector formed from an electrically conductive, rigid material including without limitation, stainless steel. Female connector 282 is electrically coupled to probe hypotube 281. Female connector 282 and/or probe hypotube 281 may be formed from any suitable electrically-conductive, high-strength, temperature resistant material, such as without limitation, stainless steel. A distal end of probe hypotube 281 includes a trocar tip 299 that has a generally tapered shape, e.g., conical, to facilitate the penetration thereof, and probe 280 generally, into tissue. A circumferential saddle 285 is defined within female connector 282 and configured to selectively operably engage rim 225 of connector 224 to facilitate the electromechanical coupling of probe 280 to handle 230. Saddle 285 and rim 225 may engage using any suitable manner of engagement, including without limitation a snap fit, interference fit, cooperating threaded engagement, or a bayonet (e.g., "half-twist") coupling. When coupled, the combination of connector 224 and connector 282 enables the conduction of electro surgical energy therethrough.

Probe 280 includes a generally tubular antenna element 293 concentrically disposed within probe hypotube 281. A proximal end of antenna element 293 includes a female barrel coupler 290 that is configured to operably engage a distal end 203 of coolant tube 202. A distal end of antenna element 293 may include a flared opening 294, though which coolant exiting from inflow conduit 287 flows into a cooling chamber 291 defined within probe hypotube 281. Barrel coupler 290 may be integrally formed with antenna element 293, by, e.g., forging, cold rolling, or machining, or may be separately fabricated and joined to antenna element 293 by, e.g., welding, brazing, soldering, crimping, and/or by threaded fastening. An o-ring 289 or other form of resilient seal is retained within barrel connector 290 to promote a fluid-tight connection between coolant tube 202 and antenna element 293, and to isolate spent coolant in and around the region of plenum 227 from the inflow conduits 207 and/or 287. Barrel connector 290 may include one or more crimps or serrations 283 configured to retain o-ring 289 in place. When antenna probe 280 is coupled to handle 230, electrosurgical energy is conducted between coolant tube 202, barrel coupler 290, and antenna element 293 to deliver electrosurgical ablation energy to targeted tissue.

One or more spacers 286 may be included within probe hypotube 281 and adapted to center antenna element 293 within hypotube 281. Spacer 286 includes one or more support legs 292 extending radially from a central hub 295. Central hub 295 is configured to retain antenna element 293 centrally within probe hypotube 281 to, e.g., define outflow conduit 288, to prevent short circuits between antenna element 293 and hypotube 281, and to promote secure engagement between barrel coupler 290 and coolant tube 202. Spacer 286 may be formed from any suitable fluid- and temperature-resistant electrically insulative material. A thermosetting polymer, such as without limitation, polyimid, may be advantageously used to form spacer 286.

Figure 12A:
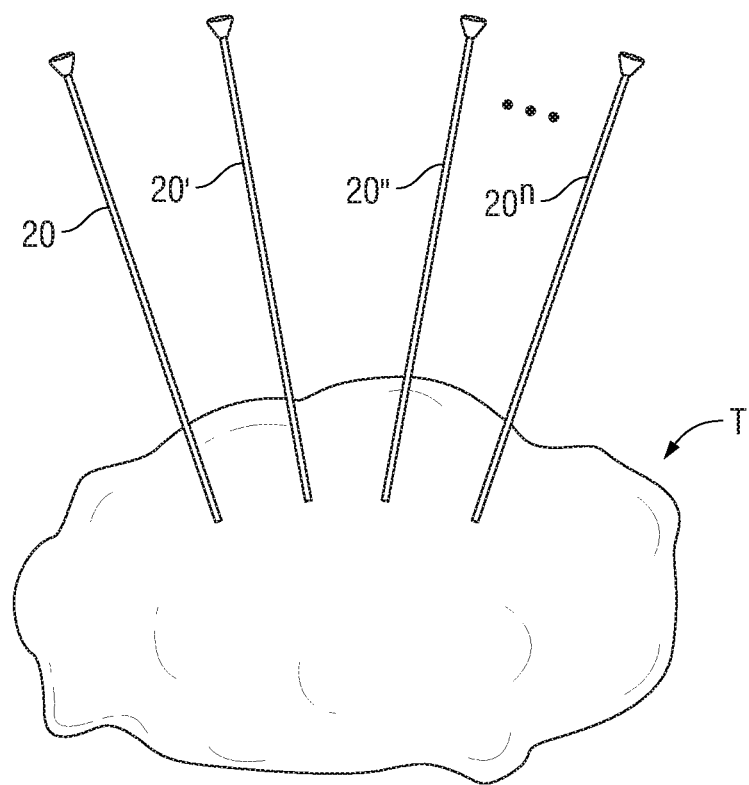
FIGS. 12A-12F show an ablation procedure performed utilizing an ablation instrument in accordance with an embodiment of the present disclosure.

Turning now to FIGS. 12A-12F, a method of performing an ablation procedure on targeted tissue T is illustrated. A surgeon determines, based on operative requirements, the number, size (e.g., length and diameter), and placement of the ablation probes 20. As shown in FIG. 12A, a plurality of probes 20, 20', 20" . . . 20" are inserted into targeted tissue T. Naturally, a greater or lesser number of probes 20 may be inserted as required, and the probes 20 may be of differing lengths and diameters as required.

Handle 30 is also operatively coupled to a generator 14 and may, additionally, be operatively coupled to a coolant source 18 as described hereinabove.

Figure 12B:
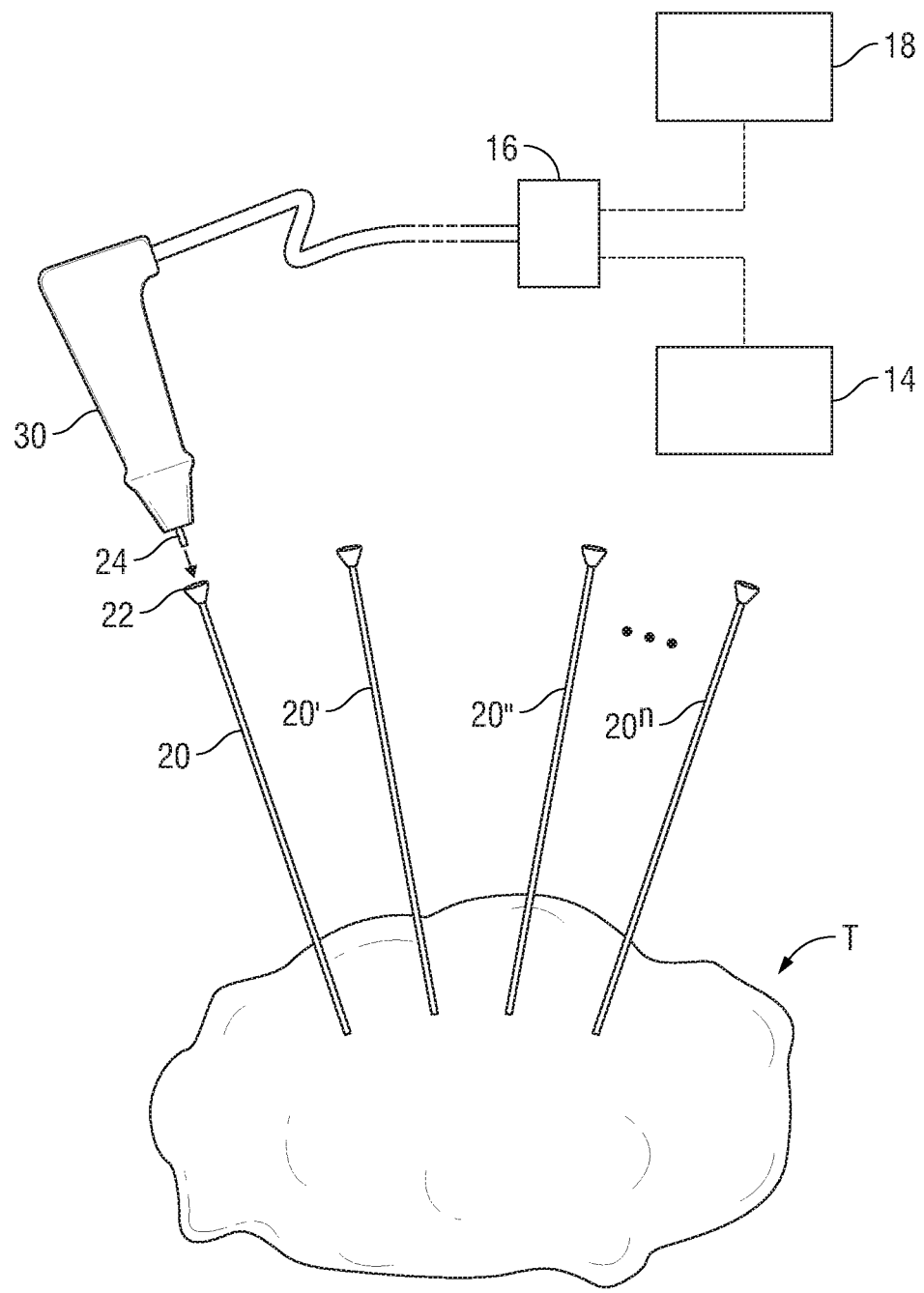
Figure 12C:
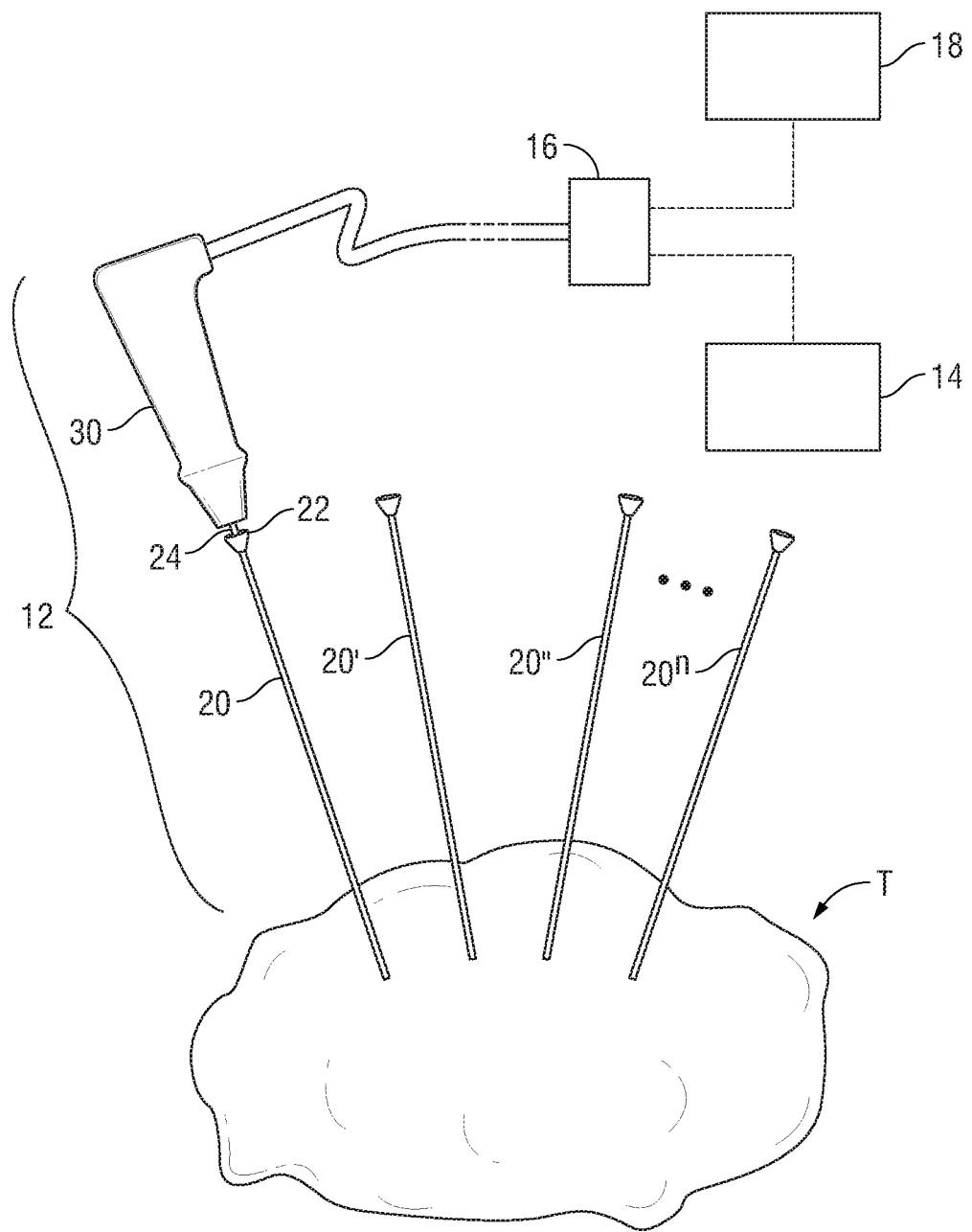

After the desired probes are positioned, a surgeon may bring a handle 30 into axial alignment with a first probe with which ablation energy is delivered to tissue T. As seen in FIGS. 12B and 12C, a surgeon aligns the handle 30 with first probe 20 such that male luer member 24 is positioned to engage female luer collar 22, mates the male luer member 24 to the female luer collar 22, and secures male luer member 24 to female luer collar 22 to form an ablation instrument 12 in accordance with the present disclosure. In various embodiments, male luer member 24 may be secured to female luer collar 22 by twisting, threading, or otherwise manipulating the engaging portions thereof accordingly to affectuate engagement.

Figure 12D:
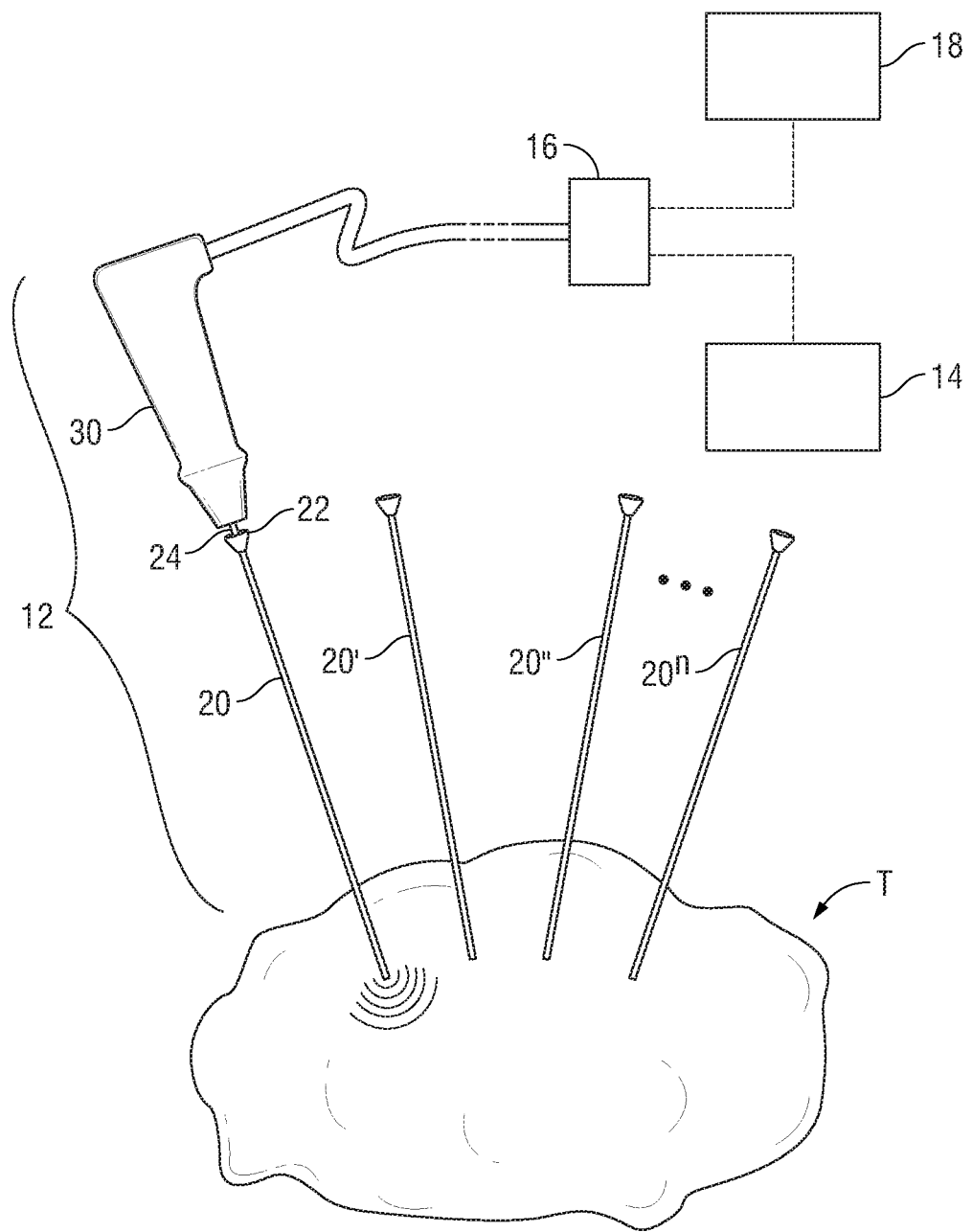
Figure 12E:
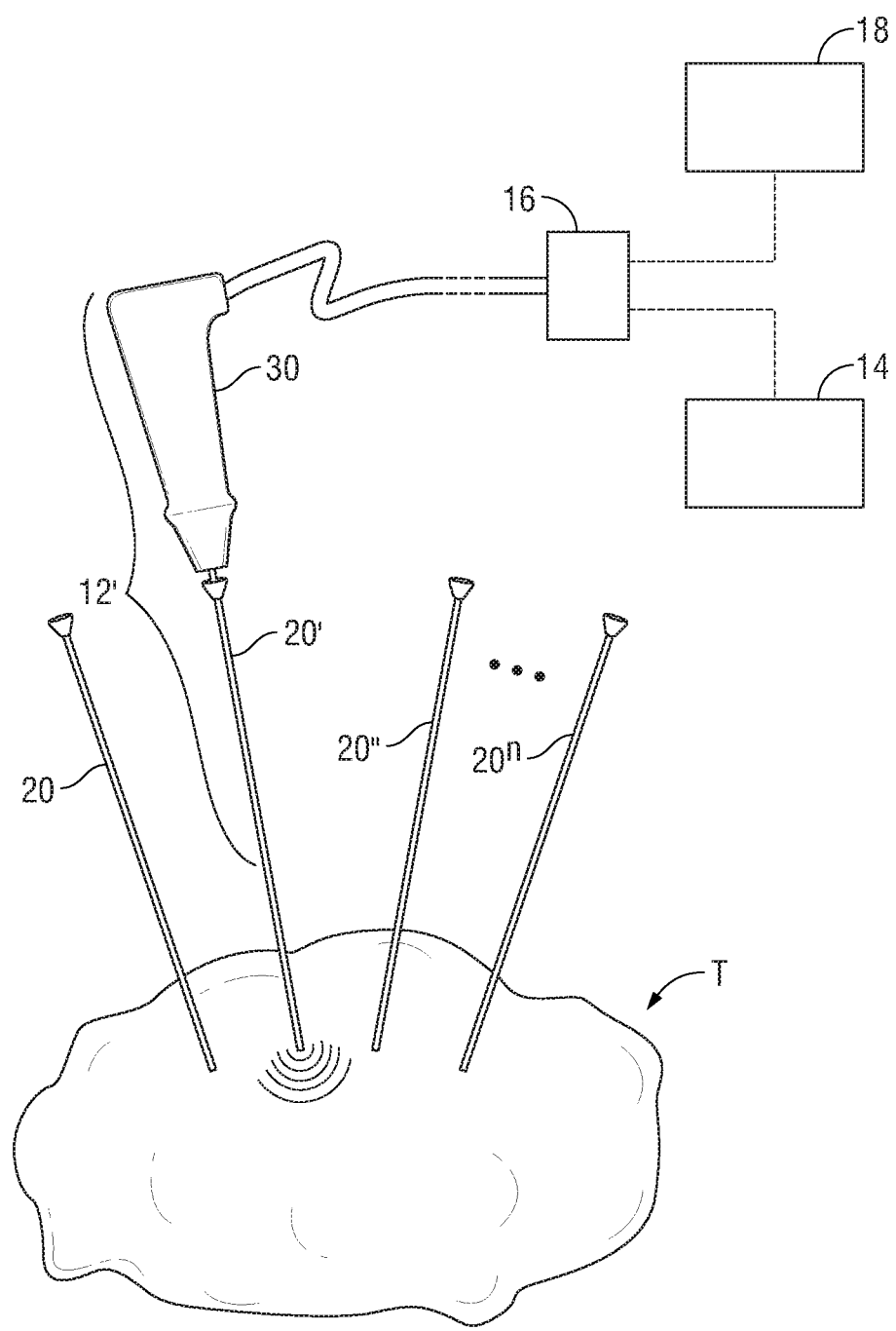
Figure 12F:
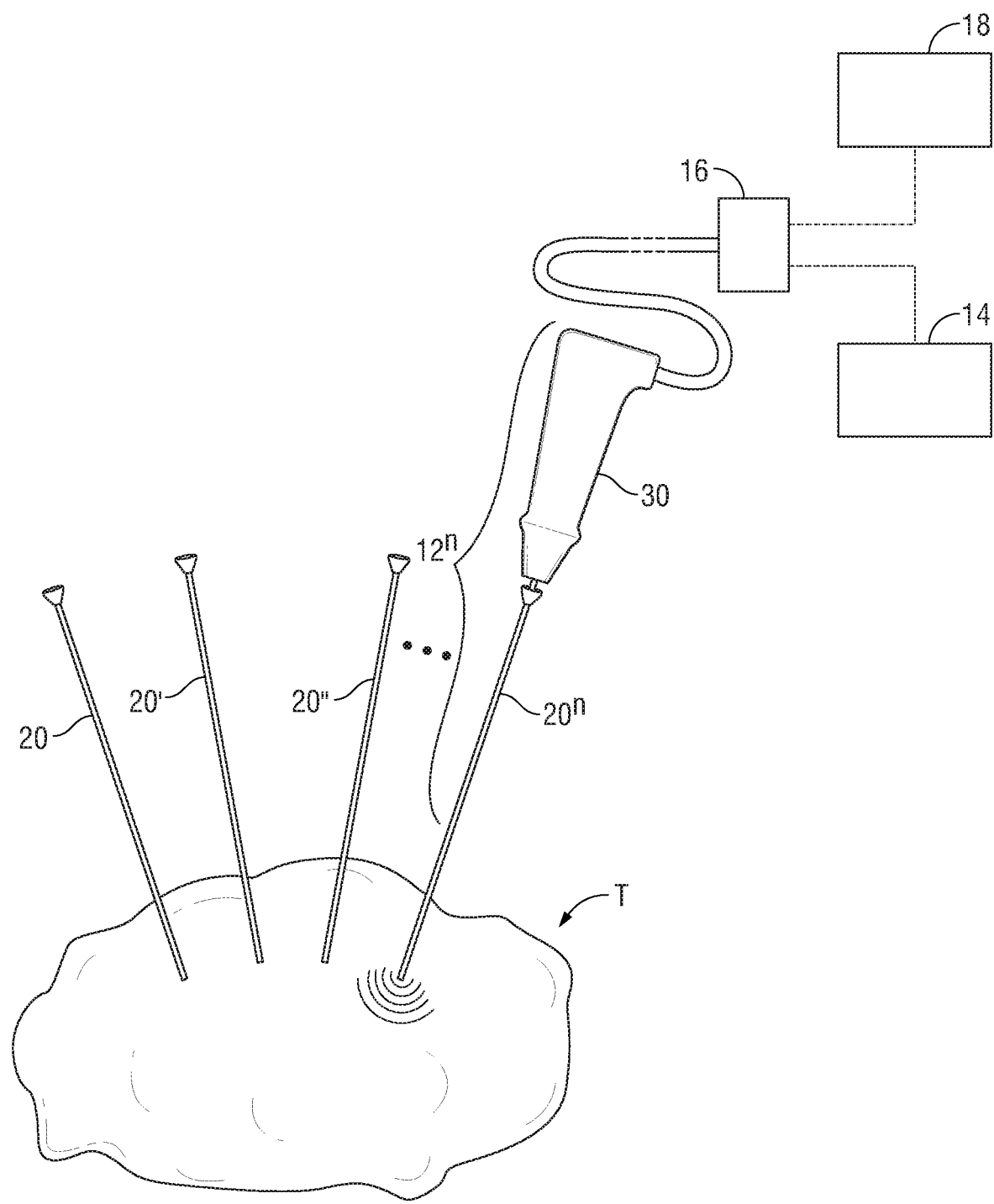

After engaging the handle 30 to the first probe 20 to form instrument 12, the surgeon may then activate the generator 14 to deliver ablation energy to tissue T as shown in FIG. 12D. The activation of generator 14 may additionally activate the delivery of coolant from coolant source 18 through instrument 12. When the desired ablation energy has been delivered to tissue, the generator 14 (and delivery of coolant, if activated) is deactivated The surgeon may then de-couple handle 30 from ablation probe 20, and couple handle 30 to a subsequent probe 20', and ablation energy applied to the second probe 20'. The procedure is repeated as required with each successive ablation probe 20" . . . 20" as illustrated by FIGS. 12E and 12F until each probe 20 et seq. has delivered ablation energy to tissue T.

The described embodiments of the present disclosure are intended to be illustrative rather than restrictive, and are not intended to represent every embodiment of the present disclosure. It is to be understood that the steps of a method provided herein may be performed in combination and/or in a different order than presented herein without departing from the scope and spirit of the present disclosure. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law.

What is claimed is:

1. A method of performing an ablation procedure, comprising:
  inserting a plurality of ablation probes into target tissue;

coupling a handle with a first ablation probe of the plurality of inserted ablation probes to form a first ablation instrument;

activating an energy source that is electrically coupled to the handle to deliver energy to the target tissue via the first ablation probe;

decoupling the handle from the first ablation probe while the first ablation probe is maintained in the target tissue; and coupling the handle to a second ablation probe of the plurality of inserted ablation probes to form a second ablation instrument.

2. The method according to claim 1, further comprising activating the energy source to deliver energy to the target tissue via the second ablation instrument.

3. The method according to claim 1, wherein coupling the handle with the first ablation probe includes forming a fluid-tight seal between a handle coolant tube of the handle and a probe coolant tube of the first inserted ablation probe.

4. The method according to claim 3, further comprising delivering cooling fluid from a coolant source to the probe coolant tube via the handle coolant tube.

5. The method according to claim 4, wherein delivering the coolant fluid includes delivering the cooling fluid into the first ablation probe via an inflow conduit extending longitudinally between the probe coolant tube and an outer conductor of the first inserted ablation probe.

6. The method according to claim 1, wherein coupling the handle with the first ablation probe includes coupling a distal portion of the handle with a proximal portion of the first inserted ablation probe to form an electrical connection between the handle and the first inserted ablation probe.

7. The method according to claim 6, further comprising:

decoupling the handle from the first ablation probe to break the electrical connection therebetween; and coupling the distal portion of the handle with a proximal portion of a second ablation probe of the plurality of inserted ablation probes to form an electrical connection between the handle and the second inserted ablation probe.

8. The method according to claim 6, wherein coupling the distal portion of the handle with the proximal portion of the first ablation probe forms a fluid-tight seal between the handle and the first ablation probe.

9. The method according to claim 1, wherein coupling the handle with the first inserted ablation probe includes receiving a distal portion of an inner conductor of the handle within an elongated cavity defined in a proximal portion of an inner conductor of the first inserted ablation probe thereby forming a detachable electrical connection between the handle and the first inserted ablation probe.

10. A method of performing an ablation procedure, comprising:

inserting a first ablation probe into target tissue;

inserting a second ablation probe into the target tissue adjacent the first ablation probe;

coupling a handle with the first inserted ablation probe to form a first ablation instrument;

activating an energy source that is electrically coupled to the handle to deliver energy to the target tissue via the first inserted ablation probe;

decoupling the handle from the first inserted ablation probe;

coupling the handle with the second inserted ablation probe to form a second ablation instrument; and activating the energy source to deliver energy to the target tissue via the second inserted ablation probe.

11. The method according to claim 10, wherein coupling the handle with the first inserted ablation probe includes forming a fluid-tight seal between a handle coolant tube of the handle and a probe coolant tube of the first inserted ablation probe.

12. The method according to claim 11, further comprising delivering cooling fluid from a coolant source to the probe coolant tube via the handle coolant tube.

13. The method according to claim 10, wherein decoupling the handle from the first inserted ablation probe breaks an electrical connection therebetween, and coupling the handle with the second inserted ablation probe forms an electrical connection therebetween.

14. The method according to claim 10, wherein decoupling the handle from the first inserted ablation probe breaks a fluid-tight seal therebetween, and coupling the handle with the second inserted ablation probe forms a fluid-tight seal therebetween.

15. The method according to claim 10, wherein coupling the handle with the first inserted ablation probe includes receiving a distal portion of an inner conductor of the handle within an elongated cavity defined in a proximal portion of an inner conductor of the first inserted ablation probe thereby forming a detachable electrical connection between the handle and the first inserted ablation probe.

16. The method according to claim 15, wherein decoupling the handle from the first inserted ablation probe includes removing the distal portion of the inner conductor of the handle from the elongated cavity defined in the proximal portion of the inner conductor of the first inserted ablation probe.

* * * * *